United States Patent
Viens et al.

(10) Patent No.: US 9,851,326 B2
(45) Date of Patent: Dec. 26, 2017

(54) ELECTROCHEMICAL SENSOR

(71) Applicant: UNIVERSITÉ LAVAL, Québec (CA)

(72) Inventors: Jean-François Viens, Québec (CA); Charles-Olivier Normandeau, Saint-Nicolas (CA); Younes Messaddeq, Québec (CA)

(73) Assignee: UNIVERSITÉ LAVAL, Québec (CA)

( * ) Notice: Subject to any disclaimer, the term of this patent is extended or adjusted under 35 U.S.C. 154(b) by 418 days.

(21) Appl. No.: 14/646,488

(22) PCT Filed: Nov. 22, 2013

(86) PCT No.: PCT/CA2013/050893
§ 371 (c)(1),
(2) Date: May 21, 2015

(87) PCT Pub. No.: WO2014/078964
PCT Pub. Date: May 30, 2014

(65) Prior Publication Data
US 2015/0338368 A1 Nov. 26, 2015

Related U.S. Application Data

(60) Provisional application No. 61/729,393, filed on Nov. 22, 2012.

(51) Int. Cl.
*G01N 27/36* (2006.01)
*G01N 27/333* (2006.01)
(Continued)

(52) U.S. Cl.
CPC ......... *G01N 27/3335* (2013.01); *G01N 27/36* (2013.01); *G01N 27/406* (2013.01);
(Continued)

(58) Field of Classification Search
CPC .. G01N 27/02–27/028; G01N 27/3335; G01N 27/4112; G01N 27/4146; G01N 27/36; G01N 27/4148; G01N 27/406
See application file for complete search history.

(56) References Cited

U.S. PATENT DOCUMENTS 4,659,435 A 4/1987 Brothers et al.
5,296,123 A 3/1994 Reddy et al.
(Continued)

FOREIGN PATENT DOCUMENTS

JP 4574847 B2 11/2010

OTHER PUBLICATIONS

Yoshida, et al. "A Hydrogen-Phosphate Ion Sensor Using Solid Electrolyte Impedance Transducer and Perovskite-Type Oxide Receptor" Electrochemistry, vol. 74, No. 2, 2006, p. 163-165.*

(Continued)

*Primary Examiner* — J. Christopher Ball
(74) *Attorney, Agent, or Firm* — Hovey Williams LLP

(57) ABSTRACT

An electrochemical ion sensor and a method for sensing a presence of at least one ion species in a solution are provided. The electrochemical sensor includes a solid-state electrolyte medium doped with an organometallic material, having an electrochemical affinity with the ion species, and a pair of electrodes electrically contacting the solid-state electrolyte. The electrochemical sensor also includes an electrical circuit configured to drive the pair of electrodes with an AC electrical excitation and to measure at least one parameter related to a complex electrical impedance of the doped solid-state electrolyte medium in response to the AC electrical excitation. The parameter may be an electrical resistance, an inductance or a combination of both, and represents the presence of the ion species in the solution when the solid-state electrolyte medium is exposed to the solution.

19 Claims, 7 Drawing Sheets

(51) Int. Cl.
*G01N 27/414* (2006.01)
*G01N 27/411* (2006.01)
*G01N 27/406* (2006.01)

(52) U.S. Cl.
CPC ..... *G01N 27/4112* (2013.01); *G01N 27/4146* (2013.01); *G01N 27/4148* (2013.01)

(56) References Cited

U.S. PATENT DOCUMENTS

| | | |
|---|---|---|
| 5,378,345 A | 1/1995 | Taylor et al. |
| 6,315,881 B1 | 11/2001 | Fu |
| 7,521,250 B2 | 4/2009 | Hamachi |
| 7,864,321 B2 | 1/2011 | Caron et al. |
| 2007/0054317 A1 | 3/2007 | Diebold et al. |
| 2007/0299617 A1 | 12/2007 | Willis |
| 2012/0187000 A1 | 7/2012 | Kahn et al. |

OTHER PUBLICATIONS

Gangali et al., "Novel monohydrogenphosphate sensor based on vanadyl salophen" Analytica chimica acta 481.1 (2003): 85-90.
The International Search Report dated Feb. 5, 2014, in PCT/CA2013/050893 filed Nov. 22, 2013.
The Written Opinion dated Jan. 29, 2014, in PCT/CA2013/050893 filed Nov. 22, 2013.

\* cited by examiner

ELECTROCHEMICAL SENSOR

RELATED APPLICATIONS

This is a national stage application under 35 U.S.C. §371 of International Application No. PCT/CA2013/050893, filed Nov. 22, 2013, which claims the benefit of U.S. Provisional Patent Application No. 61/729,393, filed Nov. 22, 2012, both of which are hereby incorporated by reference in their entireties.

FIELD OF THE INVENTION

The present invention relates to the field of electrochemical sensors, and more particularly concerns an electrochemical sensor and a method for sensing ions in a liquid or semi-liquid solution, such as nitrate, phosphate, potassium or sulfate ions.

BACKGROUND OF THE INVENTION

The increasing use of ion sensors in the field of clinical, environmental, agricultural, industrial and medicinal analysis is putting pressure on analytical chemists to develop new sensors for the fast, accurate, low-cost, reproducible and selective determination of various ion species containing nitrogen (N), phosphorus (P), potassium (K), or sulfur (S) continuously across a wide dynamic range of several orders of magnitude, i.e. from micro-molar to molar levels.

For example, due to the vital importance of phosphate in many biological, environmental and industrial systems, there is a need for phosphate-selective ion sensors for the monitoring of mono-hydrogenophosphate ($HPO_4$) or di-hydrogenophosphate ($H_2PO_4$) in aqueous solutions. The phosphate anion plays an important role in vivo. For example, in signal transmission systems, a variety of information transmissions can be controlled via the phosphate functional groups of phosphorylated proteins or phospholipids. It is therefore expected that an established sensing system for detecting phosphate anions in an aqueous solution corresponding to an in vivo environment will serve as a basic tool in cell biology and other fields for the analysis of a number of in vivo processes, the results thereof contributing to the development of new medicines and reagents. For example, the recognition of an intracellular phosphorylation signal, a key reaction for the malignant alteration caused by an abnormal information transmission, will be effective in designing inhibitors and the like against such reaction.

Existing ion sensors based on optical or potentiometric monitoring of an analyte often lack the necessary dynamic range required for the accurate and continuous determination of ion species concentration.

U.S. Pat. No. 7,864,321 (CARON) provides an optical fiber sensor wherein a chemical indicator is provided in the cladding, causing a variation of the optical absorption as a function of ion concentration in the solution. Such an optical method may suffer from intrinsic signal-to-noise limitations in the optical source/detector system, constraining the sensor to a detection dynamic range of less than three (3) orders of magnitude, which is not adapted to an accurate and continuous determination of ion species from micro-molar to molar levels. Furthermore, the broadband spectroscopic apparatus described in U.S. Pat. No. 7,864,321 tends to be very expensive.

Ganjali et al. in Analytica Chimica Acta 481 (2003) 85-90 provides for potentiometric monitoring of phosphate in aqueous solutions. Although a change of six (6) orders of magnitude in concentration of phosphate can be measured continuously, the monitoring scheme relates to a change of chemical potential in the electrolyte of only about one (1) order of magnitude. This small variation of transduction yields a large error of measurements of concentration, up to 50% measurement error, which for most applications is not adequate to the accurate determination of ion concentration in a solution.

U.S. Pat. No. 5,296,123 (REDDY) provides an electrochemical sensor adapted for use in the electrochemical analysis of liquids. The sensor performs alternating current (AC) and direct current (DC) voltammetry measurements in plating bath solutions in order to measure the electrical current through the liquid which is indicative of the quality of the electroplating solution. Although sub-milliampere electrochemical measurement methods may be adapted to provide accurate and continuous impedance readings through a large dynamic range, the sensor described in U.S. Pat. No. 5,296,123 does not provide for a selective determination of ion species containing nitrogen (N), phosphorus (P), potassium (K), or sulfur (S).

U.S. Pat. No. 7,521,250 (HAMASHI) provides a fluorescent sensor for phosphate ion and phosphorylated peptide, comprising a phosphate anion-selective fluorescent compound fluorescing at an optical wavelength of 380 nm. Although fluorescent methods provide selective monitoring schemes for ions, the intrinsic signal-to-noise limitations in optical detector systems at 380 nm constrain the sensor to a dynamic range of typically less than three (3) orders of magnitude, which is not adapted to an accurate and continuous determination of ion species from micro-molar to molar levels. Furthermore, ultraviolet (UV) optical systems capable of reliably detecting light at an optical wavelength of 380 nm tend to be very expensive.

Thus, known sensors and methods lack the full set of attributes needed for obtaining ion sensors for the fast, accurate, low-cost, reproducible and selective determination of various ion species containing nitrogen (N), phosphorus (P), potassium (K), or sulfur (S) with a wide dynamic range of several orders of magnitude, i.e. from micro-molar to molar levels. There therefore exists a need in the art for an improved electrochemical ion sensor which alleviates at least some of the drawbacks of the prior art.

SUMMARY OF THE INVENTION

According to an aspect of the invention, there is provided an electrochemical ion sensor for sensing a presence of at least one ion species in a solution. The electrochemical sensor includes, for each of the at least one ion species:
- a solid-state electrolyte medium, doped with an organometallic material, the organometallic material having an electrochemical affinity with the ion species;
- a pair of electrodes electrically contacting the solid-state electrolyte medium;
- an electrical circuit configured to drive the pair of electrodes with an AC electrical excitation and to measure at least one parameter related to a complex electrical impedance of the doped solid-state electrolyte medium in response to the AC electrical excitation, said at least one parameter being representative of the presence of the ion species in the solution when the solid-state electrolyte medium is exposed to the solution.

Preferably, the electrochemical sensor according to embodiments of the present invention, further includes, for each of the at least one ion species, a substrate supporting the corresponding solid-state electrolyte medium and pair of electrodes.

Also preferably, the electrochemical sensor according to embodiments of the present invention further includes a data processing module in communication with the electrical circuit associated with each ion species to receive therefrom the at least one parameter and determining therefrom data representative of the presence of the corresponding ion species.

According to another aspect of the invention, there is provided a method for sensing a presence of an ion species in a solution. The method includes the steps of:
a) exposing a solid-state electrolyte medium doped with an organometallic material to the solution, the organometallic material having an electrochemical affinity with the ion species;
b) driving a pair of electrodes electrically contacting the solid-state electrolyte medium with an AC electrical excitation;
c) measuring at least one parameter related to a complex electrical impedance of the solid-state electrolyte medium in response to the AC electrical excitation, the at least one parameter being representative of the presence of the ion species in the solution when the solid-state electrolyte medium is exposed to the solution.

Preferably, the method according to this aspect of the invention further includes further comprising a step d) of determining a concentration of the ion species in the solution.

According to yet another aspect of the invention, there is provided a sensing component for use in combination with an electrical circuit in an electrochemical ion sensor for sensing a presence of at least one an ion species in a solution. For each of ion species, the sensing component includes a solid-state electrolyte medium doped with an organometallic material. The organometallic material has an electrochemical affinity with the ion species. The sensing component further includes, for each ion species, a pair of electrodes electrically contacting the solid-state electrolyte medium, and a connecting interface electrically connected to the pair of electrodes and detachably connectable to the electrical circuit. The pair of electrodes is drivable by the electrical circuit, when the connecting interface is connected thereto, with an AC electrical excitation to measure at least one parameter related to a complex electrical impedance of the doped solid-state electrolyte medium in response to the AC electrical excitation. The at least one parameter is representative of the presence of the ion species in the solution when the solid-state electrolyte medium is exposed to the solution.

Other features and advantages of the present invention will be better understood upon a reading of embodiments thereof with reference to the appended drawings.

Figure 1:
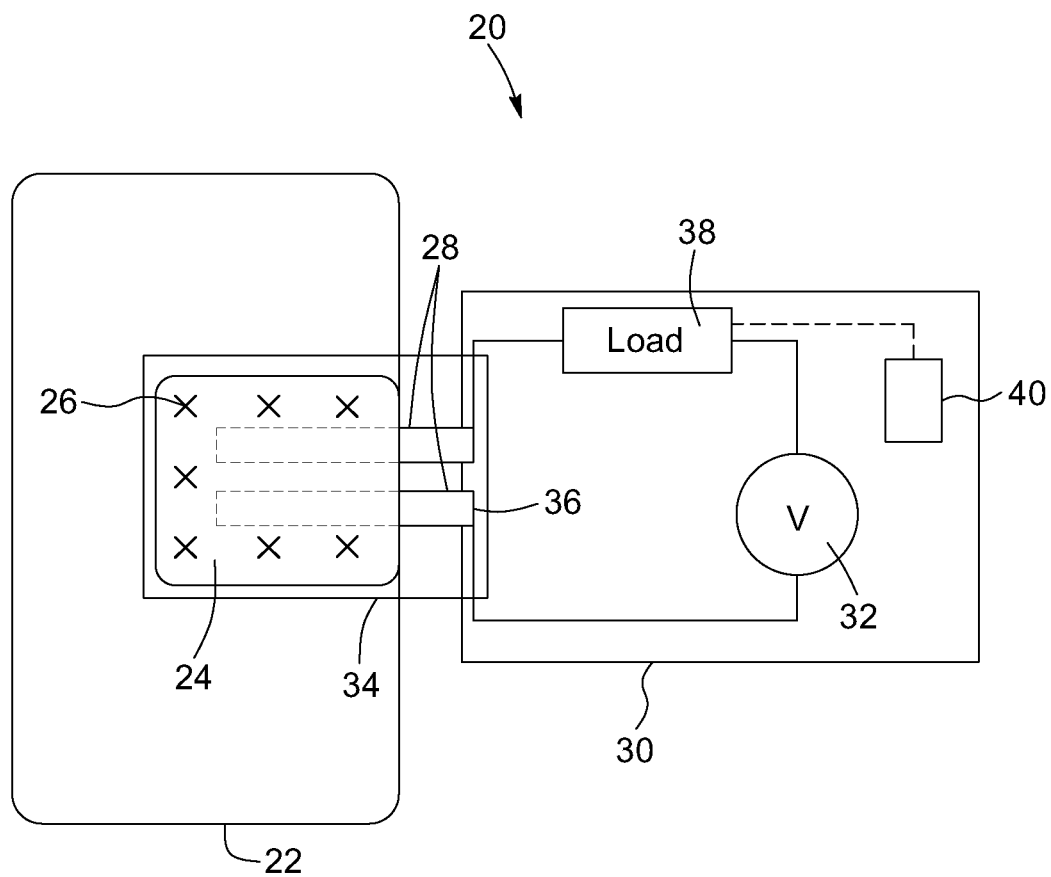
FIG. 1 schematically illustrates an electrochemical sensor for sensing a presence of at least one ion species in a solution, in accordance with an embodiment.

DESCRIPTION OF PREFERRED
EMBODIMENTS OF THE INVENTION

It is to be understood that certain descriptions of the present invention have been simplified to illustrate only those elements and limitations that are relevant to a clear understanding of the present invention, while eliminating, for purposes of clarity, other elements. Those of ordinary skill in the art, upon considering the present description of the invention, will recognize that other elements and/or limitations may be desirable in order to implement the present invention. However, because such other elements and/or limitations may be readily ascertained by one of ordinary skill upon considering the present description of the invention, and are not necessary for a complete understanding of the present invention, a discussion of such elements and limitations is not provided herein. As such, it is to be understood that the description set forth herein is merely exemplary to the present invention and is not intended to limit the scope of protection.

It is worth mentioning that throughout the following description, when the article "a" is used to introduce an element, it does not have the meaning of "only one" it rather means of "one or more".

Certain terms used in this application and their meanings as used in this context are set forth at the outset for ease of reference. To the extent a term used herein is not defined below, it should be given the broadest definition persons in the pertinent art have given that term as reflected in at least one printed publication or issued patent. Further, the present invention is not limited by the usage of the terms shown below, as all equivalents, synonyms, new developments, and terms or techniques that serve the same or a similar purpose are considered to be within the scope of the present invention.

According to an aspect of the invention, there is provided an electrochemical ion sensor for sensing a presence of at least one ion species in a solution. The solution may be a liquid or semi-liquid solution such as an aqueous solution, an acid solution, a basic solution, or other liquid solutions that may contain some amounts of solid materials therein. As used herein, the term "semi-liquid solution" is intended to refer to any substance with properties intermediate between those of a solid and a liquid. In examples of embodiments, the solution containing the ion species may include water, acid solutions, base solutions, corrosive solutions, toxic wastes, waste waters, mining byproducts, industrial byproducts, agriculture byproducts, riverbeds, marine samples, wet soil, slurries, muds, aqueous rejects, organic substances, solvents, petrol products, chemical products, biomedical samples, blood, meat, vegetables, food products, or the like.

As used herein, the term "ion" is intended to refer to an atom or molecule that carries a positive or negative electric charge as a result of having lost or gained one or more electrons. In some embodiments of the present invention, the ion species that the electrochemical sensor can detect contain nitrogen (N), phosphorus (P), potassium (K) or sulfur (S) atoms. The ions species may therefore be embodied by nitrate ($NO_3^-$) ions; phosphate ($PO_4^{3-}$), mono-hydrogenophosphate ($HPO_4^{2-}$) or di-hydrogenophosphate ($H_2PO_4^-$) ions; sulfate ($SO_4^{2-}$) ions; or $K^+$. As will be readily understood from the description below, advantageously, embodiments of the invention may allow the detection of any of these ion species over several orders of magnitude, for example from micro-molar to molar levels.

Broadly described, the electrochemical sensor includes, for each of the ion species the sensor is adapted to detect, a solid-state electrolyte medium, doped with an organometallic material, the organometallic material having an electrochemical affinity with the ion species; a pair of electrodes electrically contacting the solid-state electrolyte medium; and an electrical circuit configured to drive the pair of electrodes with an alternating-current (AC) electrical excitation and to measure at least one parameter related to a complex electrical impedance of the solid-state electrolyte medium in response to the AC electrical excitation. The parameter or parameters related to the complex impedance is representative of the presence of the ion species in the solution when the solid-state electrolyte medium is exposed to the solution.

Referring to FIG. 1, there is shown one embodiment of an electrochemical ion sensor [20] configured for sensing the presence an ion species in a solution [22]. In this embodiment, the electrochemical sensor [20] is dedicated to a single ion species, embodiments adapted for sensing more than one species being described further below.

The electrochemical ion sensor [20] includes a solid-state electrolyte medium [24] doped with an organometallic material [26]. As used herein, the term "solid-state" is intended to refer to solid phase materials as opposed to liquid or gaseous phase materials. Particularly, as used herein, the term "solid-state electrolyte" is intended to refer to a solid phase material that contains ions and that allows the diffusion flow of ions through the material. In some embodiments, the solid-state electrolyte medium [24] may be made of one or more polymer electrolyte materials, for example, polyvinyl chloride (PVC), polymethyl methacrylate (PMMA), polyvinylidene chloride (PVDC), polyvinylidene fluoride (PVDF), polydimethylsiloxane (PDMS), polyethersulfon (PES), polyethylenimine (PEI), cyclo olefin copolymer (COC), polytetrafluoroethylene (PTFE), polyimide, another polymer material, or combinations of some of the above. Alternatively or additionally, the solid-state electrolyte medium [24] may be made of glass materials, ceramic materials, semiconductor materials or combinations of some of the above. Preferably, the solid-state electrolyte medium [24] is capable of transporting ions reversibly through a diffusion process and exhibits a diffusion coefficient α of the ions thereinto of at least $\alpha=10^{-10}$ m²/s for the target ion species.

As will be readily understood by one skilled in the art, the solid-state electrolyte medium [24] may further include at least one additive. In some embodiments, the additives may be cationic or anionic additives, plasticizer materials, elastomer materials, crown ether materials, carbon nanotube materials, silane materials or combinations of some of the above. The additives may for example be provided to modify the porosity, the mechanical properties, the chemical properties, or the electrical properties of the solid-state electrolyte medium [24]. Dielectric thin-film materials (e.g. $Al_2O_3$, nitrides, oxides, polytetrafluoroethylene (PTFE), etc.) may be deposited on the solid-state electrolyte medium [24] in order to provide shielding against undesired ions (e.g. $Cl^-$, $Br^-$, etc.) or shielding against mechanical abrasion.

As mentioned above, the solid-state electrolyte medium [24] is doped with an organometallic material [26]. As used herein, the term "doped" is intended to refer to introducing impurities into a material for the purpose of modifying its electrical properties, whereas the term "organometallic" refers to a chemical compound containing bonds between carbon and a metal. The organometallic material [26] has an electrochemical affinity with the ion species. As used herein, the term "affinity" is intended to refer to chemical physics and physical chemistry, wherein affinity is the electronic property by which dissimilar chemical species are capable of forming chemical compounds. Chemical affinity can also refer to the tendency of an atom or compound to combine by chemical reaction with atoms or compounds of unlike composition. In some embodiments, the affinity of the organometallic material [26] to the ion species is chemically reversible, driven mainly by the Gibbs free energy change for the reaction and the electrochemical potential of the solid-state electrolyte medium [24]. As used herein, the term "electrochemical potential" is intended to refer to a thermodynamic measure that combines the concepts of energy stored in the form of chemical potential and electrostatics, which represents how much energy is required to add more ion species to that location. Furthermore, it will be readily understood by one skilled in the art that the term "reversible" refers to a chemical reaction that results in an equilibrium mixture of reactants and products, for which the chemical equilibrium is very sensitive to the imposed physical conditions, so the reaction can be made to run either forward or in reverse by changing those conditions. Preferably, the association of the ion with the organometallic material [26] leads to the delocalization (i.e. the donation or the acceptance) of at least one electron of the organometallic material [26] into the solid-state electrolyte medium [24].

As one skilled in the art will readily understand, the organometallic material [26] is preferably selected in view of its affinity with the ion species to be detected.

For example, the electrochemical sensor [20] may be configured for sensing the presence of phosphate ($PO_4^{3-}$) as the ion species, in which case the corresponding organometallic material [26] may contain phosphate-selective vanadyl salophen having $VO(N_2O_2)$ coordination modes.

In some embodiments, the electrochemical sensor [20] may be configured for sensing the presence of nitrate ($NO_3^-$) as the ion species. The corresponding organometallic material [26] may for example include:
  a nitrate-selective tetramethyl cyclotetra-decanato-nickel (II) complex, for example a complex based on (6,8,15,17-tetramethyl-7H,16H-5,9,14,18-tetraazidobenzo[b,i]-cyclotetra-decanato-(2-)—K4-N,N0,N00,N000)Ni (II);
  a nitrate-selective Bis(2-hydroxyanil)acetylacetone Lead (II) complex;
  a nitrate-selective cobalt(II) metallo-salen, for example a complex based on (R,R)-(–)-N,N-bis(3,5-di-tert-butyl-salicylidene)-1,2-cyclohexanediaminocobalt(II);

a nitrate-selective chromium(III) metallo-salen, for example (R,R)-(−)-N,N-bis(3,5-di-tert-butylsalicylidene)-1,2-cyclohexanediaminochromium(III) chloride;

a nitrate-selective aluminum(III) metallo-salen, for example a complex based on (R,R)—N,N-bis(3,5-di-tert-butyl-salicylidene)-1,2-cyclohexane diamino aluminum(III) chloride.

In some embodiments, the electrochemical sensor [20] may be configured for sensing the presence of sulfate ($SO_4^{2-}$) as the ion species. The corresponding organometallic material [26] may contain a sulfate-selective Zinc(II)-2,2'-[4,4'-diphenylmethane bis(nitrilomethylidyne)]-bis(phenol) complex.

It will be readily understood that the embodiments of the electrochemical sensor [20] are not limited to the specific organometallic materials [26] mentioned above, which are provided by way of example only.

Still referring to FIG. 1, in this embodiment of the present invention, the electrochemical ion sensor also includes a pair of electrodes [28] electrically contacting the solid-state electrolyte medium [24]. In some embodiments, the pairs of electrodes [28] may be made of metallic materials including aluminum, copper, chromium, gold, silver, nickel, titanium, or a combination thereof. The electrodes [28] are preferably embodied by thin films or wires capable of conducting electricity or combinations of some of the above. The electrodes [28] may be buried within the solid-state electrolyte medium [24] or extend along a surface of the solid-state electrolyte medium [24]. One skilled in the art will readily understand that the electrodes [28] may be positioned in any manner relative to the solid-state electrolyte medium [24] that allows sufficient electrical contact therebetween. The electrodes [28] may be formed through thin film deposition, lithography, screen printing, wire bonding or any other electrode [28] layout techniques known in the art. The width of the electrodes [28] may be in the range from 1 µm to 1 mm, the length may be in the range from 1 µm to 100 mm, and the spacing may be in the range from 1 µm to 10 mm. It will be readily understood that these dimensions are provided by way of example only and are not considered limitative to the scope of protection.

Preferably, the electrochemical sensor further includes a substrate [34] supporting the solid-state electrolyte medium [24] and pair of electrodes [28].

It will be readily understood that the substrate [34] may have any composition and dimensions suitable to be put in contact with the substrate [22] containing the ion species to be detected. As used herein, the term "substrate" also known in the art as a wafer, is intended to refer to a solid substance onto which a layer of another substance is applied, and to which that second substance adheres. For instance, in solid-state electronics, this term refers to a thin slice of material such as silicon, silicon dioxide, aluminum oxide, sapphire, germanium, gallium arsenide (GaAs), an alloy of silicon and germanium, or indium phosphide (InP). These serve as the foundation upon which electronic devices such as transistors, diodes, and especially integrated circuits (ICs) are deposited. Additionally, a substrate [34] in the field of electronics may either be a semiconductor or an electrical insulator, depending on the manufacturing process used.

In some embodiments, the substrate [34] may be a planar substrate including materials such as a glass, a semiconductor, a polymer, a ceramic, any other solid or semi-solid planar substrate.

Figure 7:
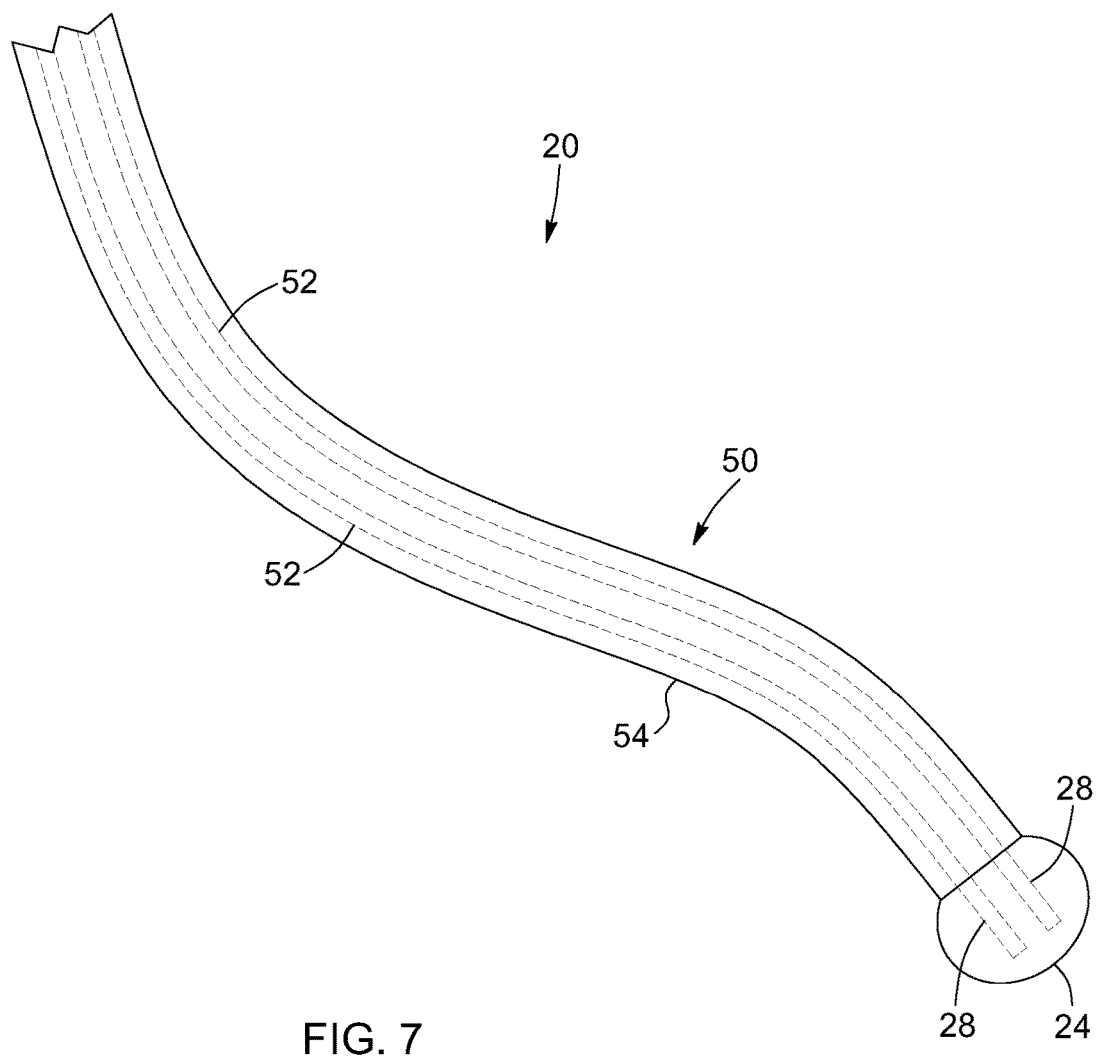
FIG. 7 schematically illustrates an electrochemical sensor for sensing a presence of one ion species in a solution, where the solid-state electrolyte medium is provided on an electrical patch cord.

Referring to FIG. 7, in some embodiments, the substrate may consist in an electrical patch cord [50] including a plurality of electrical wires [52] embedded in an insulating polymer or ceramic cladding [54]. As used herein, the term "patch cord" at times referred to as a patch cable or a patch lead, is intended to refer to a length of an electrical or optical cord with connectors on each end in order to connect an end device to a power source for instance. That is to say that, the patch cord is an electrical or optical cord used to connect an electronic or optical device to another for signal routing. In such an embodiment, the extremities of two of the electrical wires [52] of the patch cord [50] may define the pair of electrodes [28] of the electrochemical sensor. For example, the polymer or ceramic cladding of the patch cord may be partially removed to expose the electrical wires, which are then covered with the solid-state electrolyte medium 24. The solid-state electrolyte medium can form a bubble at the extremity of the patch cord, which can be exposed to the solution.

The physical area covered by the solid-state electrolyte medium [24] on the substrate [34] may be for example, from 10 µm² to 10 cm², but is not limited to dimensions within this range.

Figure 2:
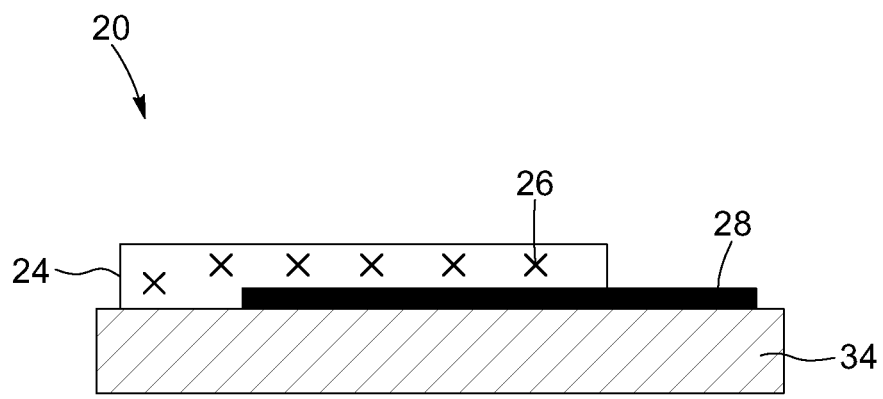
FIG. 2 is a cross-section view of a portion of the electrochemical sensor of FIG. 1.

Referring to FIG. 2, there is shown a cross-section view of the portion of the electrochemical sensor [20] of FIG. 1. In the illustrated embodiment, the electrodes [28] have been deposited on the substrate [34] through a suitable deposition technology, and the solid-state electrolyte medium [24] deposited over the electrodes [28] and surrounding portions of the substrate [34]. It will be readily understood that other configurations could be envisioned without departing from the scope of the invention.

Referring back to FIG. 1, the electrochemical ion sensor [20] further includes an electrical circuit [30]. The electrical circuit [30] is configured to drive the pair of electrodes [28] with an AC electrical excitation [32]. The expression "electrical circuit" will be understood by one skilled in the art to refer generally to a path for electrical current and no distinction is meant between "electrical circuit" and "electronic circuit". In some embodiments, the electrical circuit [30] may include an AC voltage source generating the AC electrical excitation [32]. In other embodiments, an AC current source may be used without departing from the scope of the invention. As one skilled in the art will readily understand, the letters "AC" refer to an alternating current and the AC excitation [32] may be sinusoidal, square, triangular, binary, another periodic shape or combinations of some of the above. In one example, the electronic circuit [30] may include an AC voltage source [32] working, for example, at a frequency selected between 100 hertz and 100 megahertz, or preferably between 1 kilohertz and 10 kilohertz; and impressing a voltage amplitude selected between 1 microvolt and 10 volts, or preferably between 10 millivolt and 1 volt.

The electrical circuit [30] may be connected to the pair of electrodes [28] through any mechanism allowing sufficient current flow therebetween. In one embodiment, the substrate [34] may include a connecting interface [36] associated with the pair of electrodes [28]. The interface may be embodied by an electrical connector device, or electro-mechanical connector device, for joining the pair of electrodes [28] to the electrical circuit [30] using a mechanical assembly. The connection provided by the connecting interface [36] may be temporary, permanent, keyed, or locked, the connecting interface [36] may include terminal blocks, posts, plugs, sockets, blades, rings, spades, USB connectors, or a combination thereof. The connecting interface [36] may be detachably connectable to the electrical circuit [30] or be detachably connectable to the pair of electrodes [28]. Advantageously, in such an embodiment the substrate [34] and all components thereon may be detached at the connection interface [36] from the electronic circuit [30] for replacement and disposal. Alternatively, the electrical circuit [30] and other components of the electrochemical sensor [20] may be integrally part of a same structure.

As explained above, the association of an ion with the organometallic material [26] leads to the delocalization (i.e. the donation or the acceptance) of at least one electron of the organometallic material [26] into the solid-state electrolyte medium [24]. This electron delocalization modifies the complex electrical impedance of the solid-state electrolyte medium in a manner representative of the presence of the ion species in the substrate [22] when the solid-state electrolyte medium [24] is exposed to the substrate [22]. The speed $\tau$ at which the electrochemical ion sensor [20] of embodiments of the present invention reacts to a varying level of ion concentration is related to the thickness x and diffusion coefficient $\alpha$ of the solid-state electrolyte medium [24] through the approximate relation $\tau=3x^2/\alpha$. The sensing speed $\tau$ may be a few seconds at room temperature for solid-state electrolyte medium [24] thicknesses of the order of 100 µm.

As used herein, the term "complex electrical impedance" is intended to refer to the measure of the opposition that a circuit presents to the passage of a current when a voltage is applied. More specifically, the complex electrical impedance is mathematically defined as the complex ratio of the voltage to the current in an AC circuit. Mechanisms impeding the flow of electrical current include the electrical resistance (i.e. ohmic resistance) and the electrical reactance (i.e. capacitance and inductance), where the real part of impedance is the resistance and the imaginary part of impedance is the reactance.

The complex impedance of the solid-state electrolyte medium [24] therefore involves a resistance and a reactance at the frequency of the AC voltage signal: $Z=R+jX$, where the real part of impedance is the ohmic resistance R expressed in Ohms and the imaginary part is the capacitive and/or inductive reactance X. Impedance is equivalently represented as a complex quantity Z capturing both magnitude and phase characteristics at a specific AC frequency: $Z=|Z|\exp(j\theta)$, where the magnitude $|Z|$ represents the ratio of the voltage difference amplitude to the current amplitude, while the argument $\theta$ gives the phase difference between voltage and current at the electrodes [28].

In accordance with one aspect of the invention, the electrical circuit [30] is further configured to measure at least one parameter related to the complex electrical impedance of the doped solid-state electrolyte medium [24] in response to the AC electrical excitation [32]. In different embodiments of the invention, the parameter measured may be the resistance of the solid-state electrolyte medium [24], its reactance or a combination of the resistance and the reactance.

In the embodiment of FIG. 1, the electrical circuit [30] further includes, for each of the ion species, electrical load components [38] for measuring the at least one parameter representative of the presence of the corresponding ion species. In some embodiments, the load electronic component [38] is configured to translate the measured parameter related to the complex electrical impedance into a concentration (e.g. a molar concentration) of the target ion species in the substrate [22]. Load electronic components [38] may be configured to measure the resistance, or the reactance, or both, to determine the ion species concentration in the substrate [22].

In some embodiments, the load electrical component [38] may include at least one LCR electronic circuit, at least one electronic bridge circuit such as a Wheatstone bridge, or combinations of some of the above. It will be readily understood that the electrochemical ion sensor [20] of embodiments of the present invention is not limited to these specifics. As used herein, the acronym "LCR" is intended to refer to an LCR, CRL or RLC circuit that is an electrical circuit containing a resistor, an inductor, and a capacitor, connected in series or in parallel.

Figure 3:
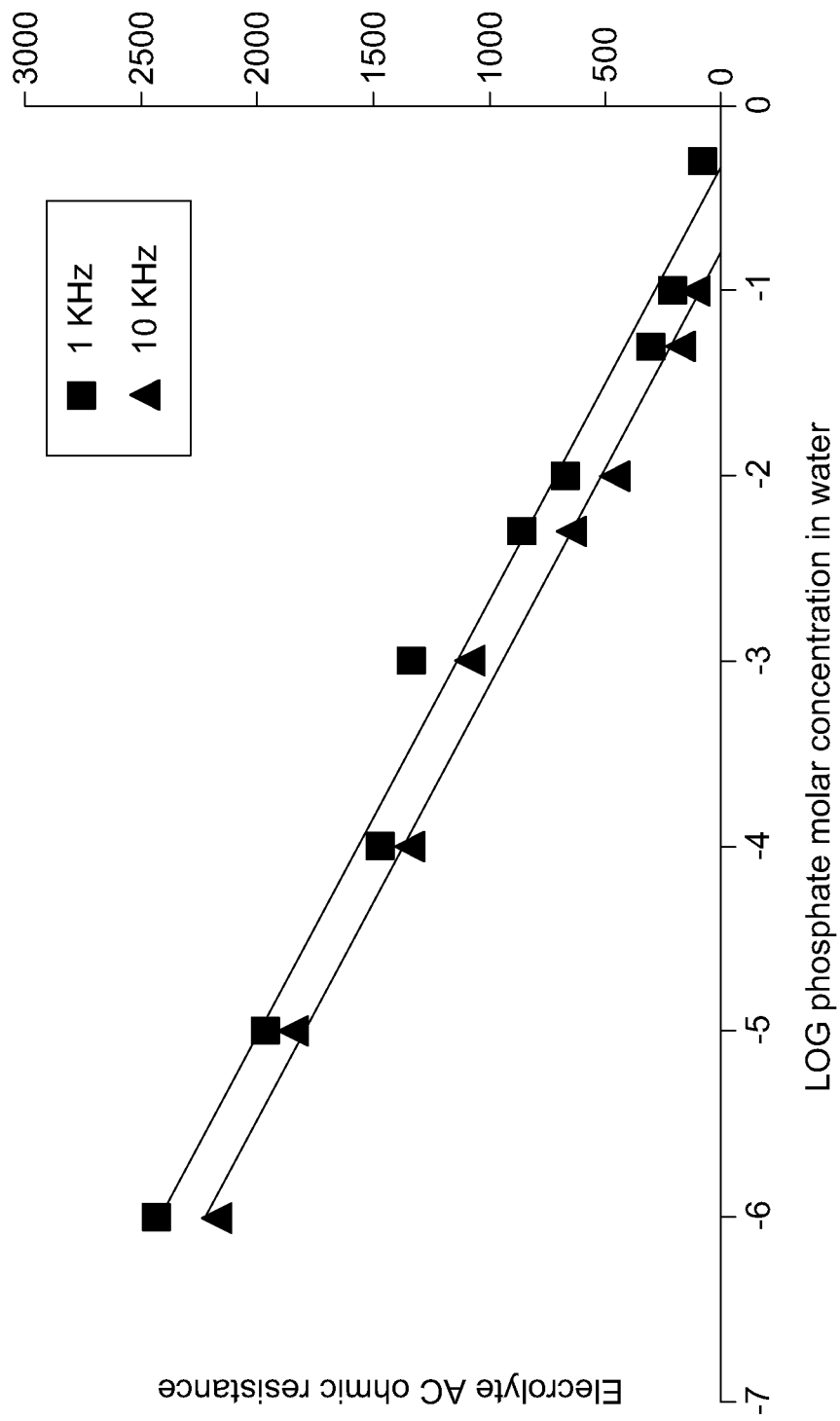
FIG. 3 shows a calibration curve that relates the ohmic resistance R of a polymer electrolyte material at frequencies of 1 kilohertz and 10 kilohertz to the molar concentration of phosphate ions in a liquid or semi-liquid solution.

Still referring to FIG. 1, in some embodiments the electrochemical sensor [20] may further includes a data processing module [40] in communication with the electrical circuit [30] to receive therefrom the parameter or parameters related to the impedance and determining therefrom data representative of the presence of the corresponding ion species. Preferably, the data representative of the presence of the corresponding ion species is a molar concentration of the ion species in the solution [22]. More preferably, the data processing module [40] determines the data in view of a calibration curve relating the measured parameters to the molar concentration. The calibration curve may for example relate the ohmic resistance R, the reactance X, the product RX, or the phase delay $\theta$, or the impedance magnitude $|Z|$ to a specific ion concentration in the aqueous substrate [22]. An example of such a calibration curve, relating the molar concentration of phosphate in water to the ohmic resistance at frequencies of 1 kilohertz and 10 kilohertz, is shown in FIG. 3. Suitable calibration curves may be obtained empirically through pre-calibration of the electrochemical sensor [20]. The data processing module [40] may include a built-in calibration curve relating the complex impedance Z at a specific AC frequency to the molar concentration of a specific ion species in the substrate [22], or the electrical circuit [30] may be connected to an external system, device or computer which stores the calibration curves and outputs the resulting information.

In other embodiments, the relation between the parameter related to complex impedance at a specific AC frequency and the molar concentration of a specific ion in a substrate [22] may be obtained or established using a theoretical model, an empirical model, or combinations of some of the above.

It will be readily understood that in some embodiments, the electrochemical sensor [20] may provide information related to the presence of the target ion species on the substrate [22] which takes a different form than the molar concentration. For example, in some embodiments the electrochemical sensor may simply provide an indication of the presence of a given ion species in the solution above a predetermined threshold. In other examples, the information provided by the electrochemical sensor may indicate the presence of a given ion species within predetermined concentration ranges.

As mentioned above, the electrochemical sensor [20] of the embodiment of FIG. 1 is dedicated to the sensing of one ion species. The illustrated electrochemical sensor [20] therefore includes one solid-state electrolyte medium [24] with the associated pair of electrodes [28] and electronic circuit [30].

Figure 4:
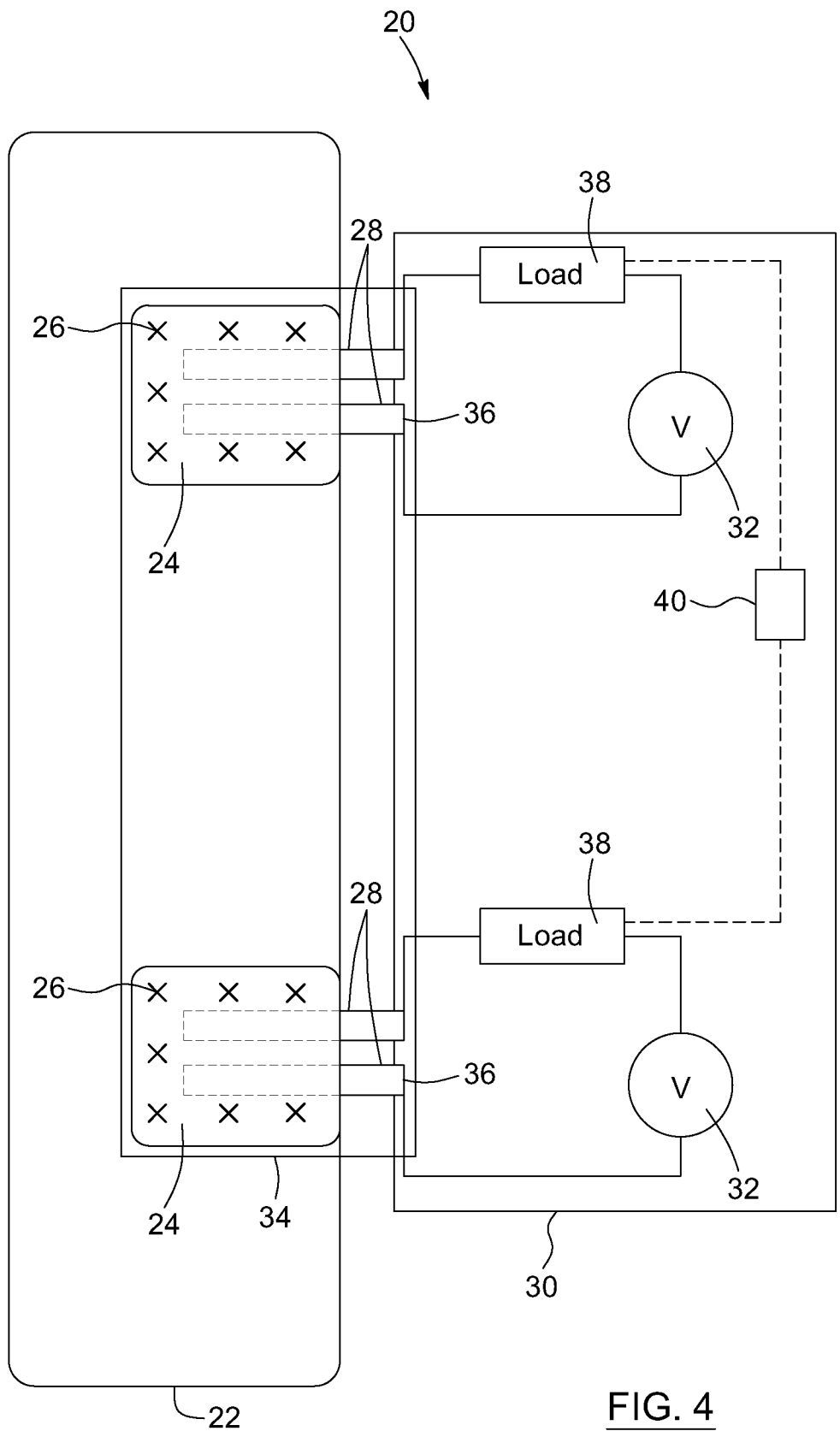
FIG. 4 schematically illustrates an electrochemical sensor for sensing a presence of at least one ion species of one or two types in a solution, in which the two solid-state electrolyte media are provided on a common substrate.
Figure 5:
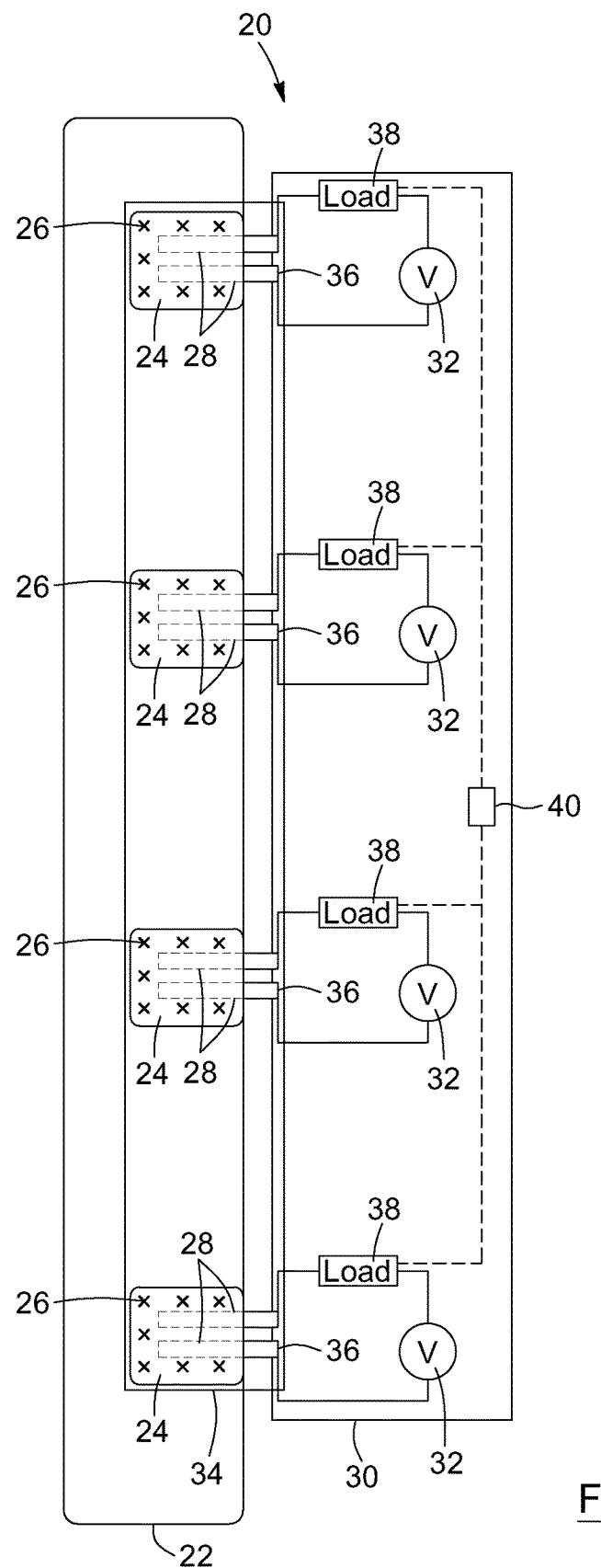
FIG. 5 schematically illustrates an electrochemical sensor for sensing a presence of at least one ion species up to four different types in a solution, in which the four solid-state electrolyte media are provided on a common substrate.

In other embodiments, the electrochemical sensor [20] may be configured for sensing a plurality of the ion species. In this case, a specific solid-state electrolyte medium [24] and pair of electrodes [28] are provided for each ion species. Referring to FIGS. 4 and 5, embodiments of electrochemical sensors [20] including one substrate [34] supporting the solid-state electrolyte medium [24] and the pair of electrodes

[28] associated with all of the species are shown. In the embodiment of FIG. 4, two solid-state electrolyte media [24] are shown on the common substrate [34], whereas FIG. 5 shows a variant with four solid-state electrolyte media [24]. Each solid-state electrolyte medium [24] may be dedicated to one ion species of interest. Preferably different solid-state electrolyte media [24] are doped with different organometallic materials [26] such that they are sensitive to different ion species. For example, the embodiment of FIG. 5 may provide a full NPKS sensing capability by providing each of the four solid-state electrolyte media [24] with an organometallic material [26] with an affinity with ion species containing nitrogen (N), phosphorus (P), potassium (K), or sulfur (S) atoms, respectively. In other variants, two or more solid-state electrolyte media [24] of a same sensor [20] may be dedicated to the sensing of a same ion, to provide an increased accuracy or redundancy of the measures. The substrate [34] may be detachable from the electrical circuit [30] dedicated to each ion species through an appropriate connecting interface [36], as explained above.

It will be understood by those skilled in the art that various changes in form and details may be made therein to scale embodiments of the invention to the sensing of up to four ion species selected from the nitrogen (N), phosphorus (P), potassium (K), or sulfur (S) ion species. Such NPKS electrochemical sensor [20], integrating nitrate, phosphate, potassium and sulfate ion sensing capabilities, may include one, two, three or four detachable substrates [34]. It will be further understood that although the illustrated embodiments show a dedicated electrical circuit [30] associated with each solid-state electrolyte medium [24], in another variants one or a smaller number of electrical circuits [30] may be provided and various changes may be made to the electronic circuit or circuits [30] to configure them to measure the complex electrical impedance of any corresponding solid-state electrolyte medium [24], without departing from the scope of the invention.

Figure 6:
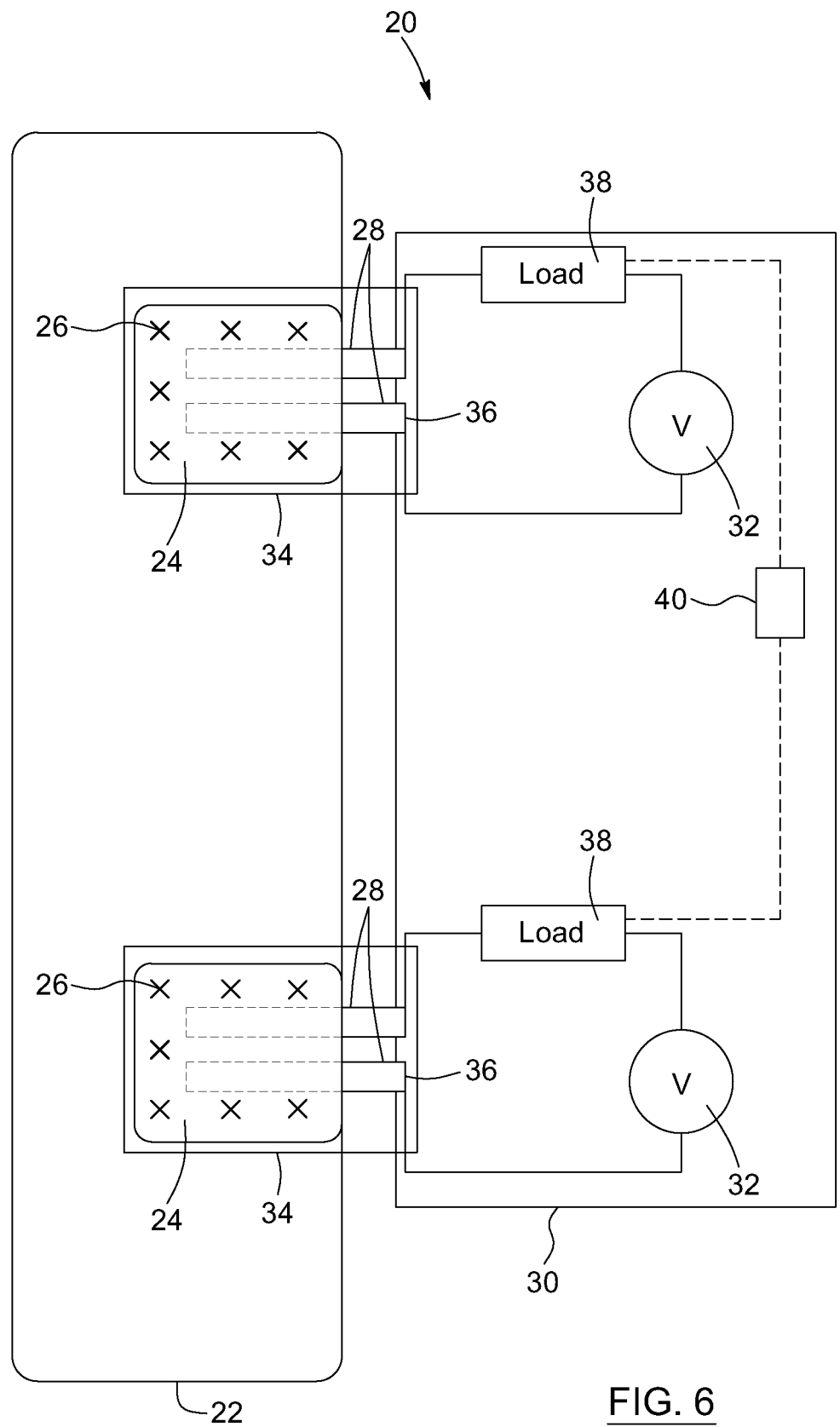
FIG. 6 schematically illustrates an electrochemical sensor for sensing a presence of at least one ion species of one or two types in a solution, in which two solid-state electrolyte media each provided on individual substrates.

Of course, in other embodiment each selectively-doped solid-state electrolyte medium [24] and the corresponding electrodes [28] may be provided on a different substrate [34], or arranged in various sub combinations on different substrates [34], without departing from the scope of the present invention. For example, FIG. 6 shows a variant having two solid-state electrolyte media [24] each provided on an individual substrate [34].

In accordance with an aspect of the invention, the solid-state electrolyte medium, and electrodes on a suitable substrate and the corresponding connecting interface may defined a sensing component provided separately from the electrical circuit to form the electrochemical sensor described above. Although the sensing mechanism described herein is reversible and a same solid-state electrolyte medium may be re-used for testing different solutions, it may be desired to provide replacement sensing components, or to provide kits of sensing components for various ions species adapted to interface with a pre-existing electrical circuit.

Figure 8:
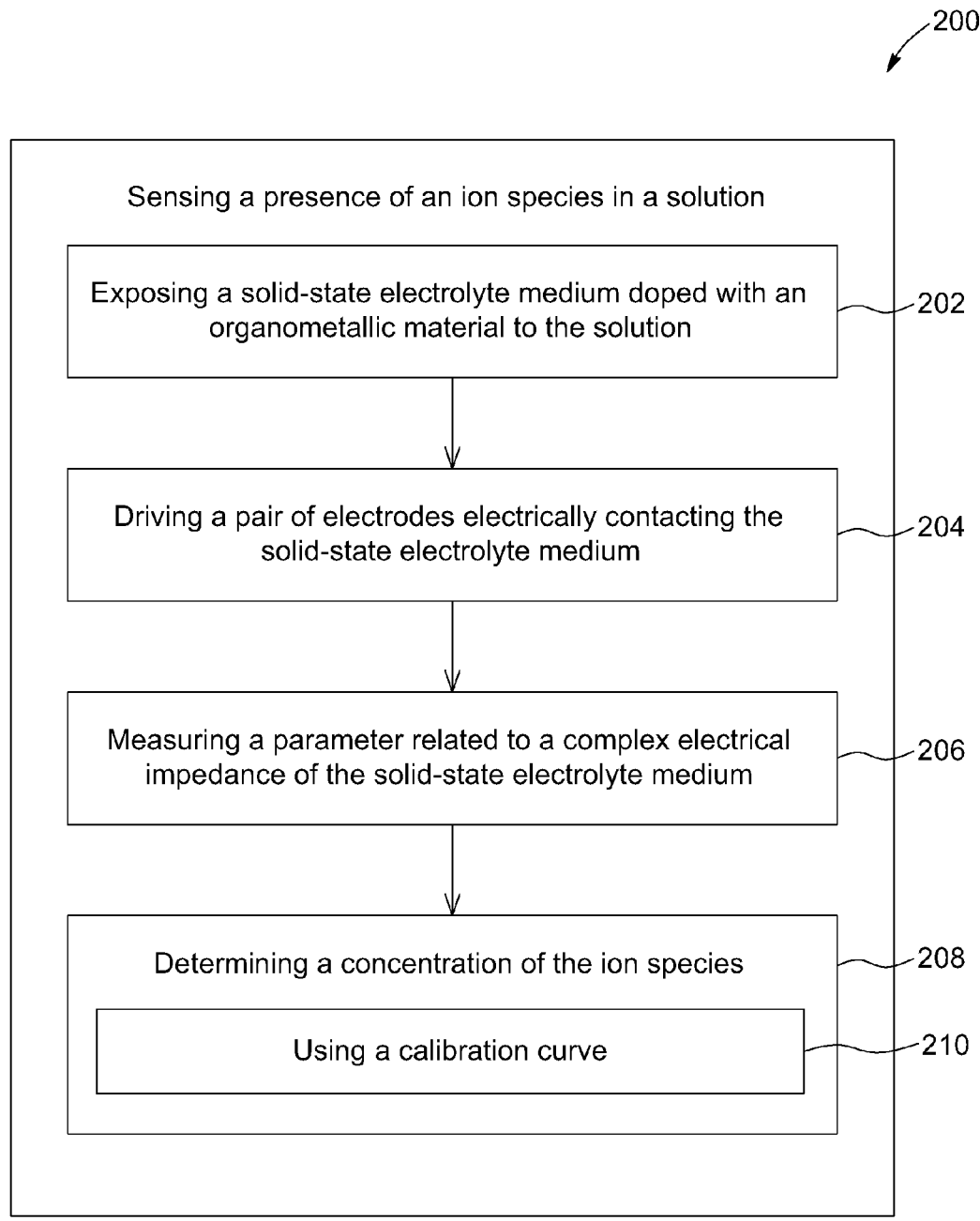
FIG. 8 is a flow chart of a method for sensing a presence of an ion species in a solution, in accordance with an embodiment of the invention.

According to a further aspect of the present invention, there is provided a method for sensing a presence of an ion species in a solution. FIG. 8 shows a flow chart of an embodiment of the method [200], which could, by way of example, be performed for sensing a presence of an ion species such as that illustrated in FIG. 1.

Referring to FIG. 8, the method [200] according to this aspect of the invention includes a first step of exposing [202] a solid-state electrolyte medium doped with an organometallic material to the solution, the organometallic material having an electrochemical affinity with the ion species. The solid-state electrolyte medium may have any of the characteristics described above with respect to electrochemical sensors accord to embodiments of the invention. Preferably, the ion species include one of nitrogen (N), phosphorus (P), potassium (K) and sulfur (S) atoms.

In some embodiments, the ion species according to the method [200] may include phosphate, and the organometallic material may contain phosphate-selective vanadyl salophen having $VO(N_2O_2)$ coordination modes.

In some other embodiments, the ion species according to the method [200] may include nitrate, and the organometallic material may contain one of:
  a nitrate-selective tetramethyl cyclotetra-decanato-nickel (II) complex;
  nitrate-selective Bis(2-hydroxyanil)acetylacetone Lead (II) complex;
  a nitrate-selective cobalt(II) metallo-salen complex;
  a nitrate-selective chromium(III) metallo-salen complex; or
  a nitrate-selective aluminum(III) metallo-salen complex.

In yet some other embodiments, the ion species according to the method [200] may include sulfate, and the organometallic material may contain a sulfate-selective Zinc(II)-2, 2'-[4,4'-diphenylmethane bis(nitrilomethylidyne)]-bis(phenol) complex.

The method next includes a step of driving [204] a pair of electrodes electrically contacting the solid-state electrolyte medium with an AC electrical excitation. The electrodes may have some of the characteristics described above, and an electrical circuits as also described herein may be used to apply the AC electrical excitation.

The method next includes a step of measuring [206] at least one parameter related to a complex electrical impedance of the solid-state electrolyte medium in response to the AC electrical excitation, the at least one parameter being representative of the presence of the ion species in the solution when the solid-state electrolyte medium is exposed to the solution. This parameter may include an electrical resistance value, a reactance value or combinations of the above. The measuring of such parameters can be made by any method described herein or otherwise known in the art.

In some embodiments, the method [200] may further include a step d) of determining [208] a concentration of the ion species in the solution. For example, a calibration curve [210] relating the at least one parameter related to the complex impedance to the concentration of the ion species may be used in this process.

It will be understood by those skilled in the art that the method [200] according to embodiments of the present invention may be performed sequentially or simultaneously for sensing the presence of the ion species in the solution. For example, in one embodiment, the method [200] may be performed to determine simultaneously and independently the concentration of ionic species containing one of nitrogen (N), phosphorus (P), potassium (K) and sulfur (S) atoms.

While this invention has been particularly shown and described with references to preferred embodiments thereof, it will be understood by those skilled in the art that various changes in form and details may be made therein without departing from the scope of the invention encompassed by the appended claims.

The invention claimed is:
1. An electrochemical ion sensor for sensing a presence of at least one ion species in a solution, the electrochemical sensor comprising, for each of said at least one ion species:

a) a solid-state electrolyte medium, doped with an organometallic material, the organometallic material having an electrochemical affinity with the ion species;

b) a pair of electrodes electrically contacting the solid-state electrolyte medium; and c) an electrical circuit configured to drive the pair of electrodes with an AC electrical excitation and to measure at least one parameter related to a complex electrical impedance of said doped solid-state electrolyte medium in response to the AC electrical excitation, said at least one parameter being representative of the presence of the ion species in said solution when the solid-state electrolyte medium is exposed to the solution.

2. The electrochemical sensor according to claim 1, wherein the solid-state electrolyte medium comprises a polymer material, a glass material, a ceramic material, a semiconductor material or a combination thereof.

3. The electrochemical sensor according to claim 1, wherein the solid-state electrolyte medium further comprises at least one additive, the at least one additive comprising at least one of a cationic additive, an anionic additive, a plasticizer material, an elastomer material, a crown ether material, a carbon nanotube material or a silane material.

4. The electrochemical sensor according to claim 1, configured for sensing the presence of phosphate as one of said at least one ion species, the corresponding organometallic material consisting of phosphate-selective vanadyl salophen having $VO(N_2O_2)$ coordination modes.

5. The electrochemical sensor according to claim 1, configured for sensing the presence of nitrate as one of said at least one ion species, the corresponding organometallic material consisting of one of:

a) a nitrate-selective tetramethyl cyclotetra-decanato-nickel(II) complex;

b) a nitrate-selective Bis(2-hydroxyanil)acetylacetone Lead(II) complex;

c) a nitrate-selective cobalt(II) metallo-salen complex;

d) a nitrate-selective chromium(III) metallo-salen complex; and e) a nitrate-selective aluminum(III) metallo-salen complex.

6. The electrochemical sensor according to claim 5, wherein a) the nitrate-selective tetramethyl cyclotetra-decanato-nickel(II) complex is (6,8,15,17-tetramethyl-7H,16H-5,9,14,18-tetraazidobenzo [b,i]-cyclotetra-decanato-(2-)-K4-N,N0,N00,N000) Ni(II);

b) the nitrate-selective cobalt(II) metallo-salen complex is (R,R)-(−)-N,N-bis(3,5-di-tert-butylsalicylidene)-1,2-cyclohexanediaminocobalt(II);

c) the nitrate-selective chromium(III) metallo-salen complex is (R,R)-(−)-N,N-bis(3,5-di-tert-butylsalicylidene)-1,2-cyclohexanediaminochromium(III) chloride; and d) the nitrate-selective aluminum(III) metallo-salen complex is (R,R)-N,N-bis(3,5-di-tert-butyl-salicylidene)-1,2-cyclohexane diamino aluminum(III) chloride.

7. The electrochemical sensor according to claim 1, configured for sensing the presence of sulfate as one of said at least one ion species, the corresponding organometallic material consisting of a sulfate-selective Zinc(II)-2,2'-[4,4'-diphenylmethane bis(nitrilomethylidyne)]-bis(phenol) complex.

8. The electrochemical sensor according to claim 1, wherein the electrodes are buried within the solid-state electrolyte medium.

9. The electrochemical sensor according to claim 1, further comprising, for each of said at least one ion species, a substrate supporting the corresponding solid-state electrolyte medium and pair of electrodes.

10. The electrochemical sensor according to claim 9, wherein the substrate comprises an electrical patch cord having at last two electrical wires defining the pair of electrodes.

11. The electrochemical sensor according to claim 1, wherein, for each of said ion species, the electrical circuit comprises a load electrical component for measuring at least one parameter representative of the presence of the corresponding ion species, the load electrical component comprises at least one LCR electronic circuit, at least one electronic bridge circuit or a combination thereof.

12. The electrochemical sensor according to claim 1, wherein, for at least one of said ion species, at least one parameter representative of the presence of the corresponding ion species is a resistance, a reactance or a combination of the resistance and the reactance of the corresponding solid-state electrolyte medium in response to the AC electrical excitation.

13. A method for sensing a presence of an ion species in a solution, the method comprising the steps of:

a) exposing a solid-state electrolyte medium doped with an organometallic material to the solution, the organometallic material having an electrochemical affinity with the ion species;

b) driving a pair of electrodes electrically contacting the solid-state electrolyte medium with an AC electrical excitation; and c) measuring at least one parameter related to a complex electrical impedance of said solid-state electrolyte medium in response to the AC electrical excitation, said at least one parameter being representative of the presence of the ion species in said solution when the solid-state electrolyte medium is exposed to the solution.

14. The method according to claim 13, wherein the ion species comprises one of nitrogen (N), phosphorus (P), potassium (K) and sulfur (S) atoms.

15. The method according to claim 13, wherein said ion species comprises i) phosphate, and the organometallic material consists of phosphate-selective vanadyl salophen having $VO(N_2O_2)$ coordination modes ii) nitrate, and the organometallic material consists of one of a nitrate-selective tetramethyl cyclotetra-decanato-nickel(II) complex, a nitrate-selective Bis(2-hydroxyanil)acetylacetone Lead(II) complex, a nitrate-selective cobalt(II) metallo-salen complex;a nitrate-selective chromium(III) metallo-salen complex, and a nitrate-selective aluminum(III) metallo-salen complex; or iii) sulfate, and the organometallic material consists of a sulfate-selective Zinc(II)-2,2'-[4,4'-diphenylmethane bis(nitrilomethylidyne)]-bis(phenol) complex.

16. The method according to claim 13, further comprising a step d) of determining a concentration of the ion species in the solution.

17. A sensing component for use in combination with an electrical circuit in an electrochemical ion sensor for sensing a presence of at least one an ion species in a solution, the sensing component comprising, for each of said at least one ion species:

i) a solid-state electrolyte medium, doped with an organometallic material, the organometallic material having an electrochemical affinity with the ion species;

ii) a pair of electrodes electrically contacting the solid-state electrolyte medium; and iii) a connecting interface electrically connected to the pair of electrodes and detachably connectable to the electrical circuit;

whereby the pair of electrodes is drivable by the electrical circuit, when the connecting interface is connected thereto, with an AC electrical excitation to measure at least one parameter related to a complex electrical impedance of said doped solid-state electrolyte medium in response to the AC electrical excitation, said at least one parameter being representative of the presence of the ion species in said solution when the solid-state electrolyte medium is exposed to the solution.

18. The sensing component according to claim 17, wherein said ion species comprises i) phosphate, and the organometallic material consists of phosphate-selective vanadyl salophen having $VO(N_2O_2)$ coordination modes ii) nitrate, and the organometallic material consists of one of a nitrate-selective tetramethyl cyclotetra-decanato-nickel(II) complex, a nitrate-selective Bis(2-hydroxyanil)acetylacetone Lead(II) complex, a nitrate-selective cobalt(II) metallo-salen complex; a nitrate-selective chromium(III) metallo-salen complex, and a nitrate-selective aluminum(III) metallo-salen complex; or iii) sulfate, and the organometallic material consists of a sulfate-selective Zinc(II)-2,2'-[4,4'-diphenylmethane bis(nitrilomethylidyne)]-bis(phenol) complex.

19. The sensing component according to claim 17, further comprising, for each of said at least one ion species, a substrate supporting the corresponding solid-state electrolyte medium and pair of electrodes.

* * * * *